United States Patent [19]
Öhlschläger et al.

[11] Patent Number: 4,810,627
[45] Date of Patent: Mar. 7, 1989

[54] PHOTOGRAPHIC RECORDING MATERIAL

[75] Inventors: Hans Öhlschläger, Bergisch Gladbach; Walter Pätzold, Leverkusen; Helmut Reuss, Bergisch Gladbach, all of Fed. Rep. of Germany; Karl Steinbeck, Leawood, Kans.

[73] Assignee: Agfa-Gevaert Aktiengesellschaft, Leverkusen, Fed. Rep. of Germany

[21] Appl. No.: 169,971

[22] Filed: Mar. 18, 1988

[30] Foreign Application Priority Data

Apr. 1, 1987 [DE] Fed. Rep. of Germany ....... 3710956

[51] Int. Cl.⁴ ................................................. G03C 1/34
[52] U.S. Cl. ..................................................... 430/611
[58] Field of Search .................................. 430/611, 600

[56] References Cited

U.S. PATENT DOCUMENTS 3,929,786 12/1975 Rickter ................................ 430/243
4,148,657 4/1979 Beretta et al. ...................... 430/611

Primary Examiner—Won H. Louie
Attorney, Agent, or Firm—Connolly & Hutz

[57] ABSTRACT

Compounds corresponding to the formula:

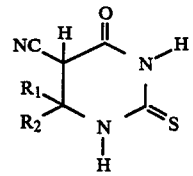

wherein $R_1$ and $R_2$ denote alkyl groups with 1 to 8 carbon atoms, an optionally substituted alkenyl group with 2 to 5 carbon atoms, an optionally substituted cycloalkyl group with 5 or 6 carbon atoms or an optionally substituted aryl group or $R_1$ and $R_2$ together represent the ring members required to form a 5- or 6-membered cycloalkyl or cycloalkenyl group, are suitable for use as antifoggants in photographic recording materials.

2 Claims, No Drawings

PHOTOGRAPHIC RECORDING MATERIAL

This invention relates to a photographic recording material containing at least one silver halide emulsion layer and optionally other layers and an antifoggant. According to the invention, the material contains a compound corresponding to the formula:

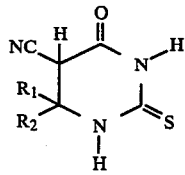

wherein $R_1$ and $R_2$ denote an optionally substituted alkyl group with 1 to 8 carbon atoms, in particular methyl, ethyl, propyl, isopropyl or butyl, an optionally substituted alkenyl group with 2 to 5 carbon atoms, e.g. an allyl group, an optionally substituted cycloalkyl group with 5 or 6 carbon atoms, such as cyclohexyl, or an optionally substituted aryl group such as phenyl or $R_1$ and $R_2$ together denote the ring members required to form a 5- or 6-membered cycloalykyl or cycloalkenyl group, e.g. the members required to form a cyclopentyl, cyclohexyl or 3-cyclohexenyl ring.

The substituents in groups $R_1$ and $R_2$ are suitably those conventionally used in photographic antifoggants, such as halogens, in particular chlorine or bromine, $C_1$-$C_4$-alkoxy groups, or di-$C_1$-$C_4$-alkyl-substituted amino groups, e.g. diethylamino or $C_1$-$C_4$-alkylthio such as methylthio. The cycloalkyl groups and aryl groups may also be substituted by $C_1$-$C_4$-alkyl.

$R_1$ preferably stands for a $C_1$-$C_4$-alkyl group and $R_2$ for a $C_1$-$C_4$-alkyl, phenyl, cyclohexyl, di-$C_1$-$C_4$-alkylamino-$C_1$-$C_4$-alkyl, $C_1$-$C_4$-alkoxy-$C_1$-$C_4$-alkyl, $C_1$-$C_4$-alkylthio-$C_1$-$C_4$-alkyl or allyl or together they denote tetramethylene or pentamethylene.

The following are suitable examples of the compounds according to this invention:

| No. | $R_1$ | $R_2$ |
| --- | --- | --- |
| 1 | $CH_3$ | $CH_3$ |
| 2 | $CH_3$ | $CH_2$—$CH$=$CH_2$ |
| 3 | $CH_3$ | phenyl |
| 4 | $CH_3$ | $(CH_2)_3$—$N(C_2H_5)_2$ |
| 5 | $C_2H_5$ | $C_2H_5$ |
| 6 | $CH_3$ | $CH_2$—$S$—$CH_3$ |
| 7 | | —$(CH_2)_4$— |
| 8 | | —$(CH_2)_5$— |
| 9 | $CH_3$ | cyclohexyl |

Compounds corresponding to the following formulae are comparison compounds:

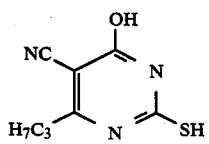

This compound shows that it is not the cyano substitutents but the transition to the non-aromatic system which is decisive for the invention.

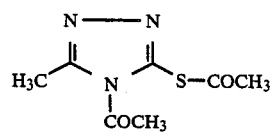

U.S. Pat. No. 4 396 707

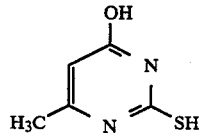

U.S. Pat. No. 2 232 707

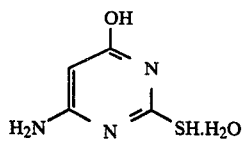

U.S. Pat. No. 2 304 962

The compounds according to the invention may be prepared by the condensation of cyanoacetic esters and thiourea with a ketone with the addition of a base, as described by S. Kambe et al., in Synthesis 1979, page 287. This is illustrated by way of example with reference to compound No. 7:

A mixture of 22.6 g of cyanoacetate, 18.4 g of cyclopentanone and 15.2 g of thiourea in 50 ml of acetonitrile is heated under reflux with 13 g of caustic potash for 2 hours. The mixture is cooled and the product is suction filtered, dissolved in 120 ml of water, filtered from the slight residue and precipitated with glacial acetic acid. After suction filtration and recrystallisation from methanol, 16.8 g of colourless product melting at 226° to 227° C. are obtained.

The photographic recording materials used may be colour negative films, colour reversal films, colour positive films, colour photographic paper, colour reversal photographic paper, colour sensitive materials for the dye diffusion transfer process or a silver dye bleaching process and black-and-white light-sensitive materials such as black-and-white films, X-ray films, process films, black-and-white photographic paper, films for aerial photography, microfilms, facsimile films, films and photographic paper for photo compositions, films for graphic work, etc.

The light-sensitive silver halide emulsions may be emulsions of silver chloride, silver bromide or mixtures thereof, possibly with a silver iodide content of up to 12 mol-%, in gelatine although the latter may be partly replaced by other natural or synthetic binders.

In colour photographic recording materials, the emulsions may be chemically and spectrally sensitized in the usual manner.

The silver halide emulsions may also contain conventional stabilizers such as azaindenes, e.g. 4-hydroxy-6-methyl-1,3,3a,7-tetraazaindene.

Colour photographic recording materials conventionally contain at least one silver halide emulsion layer for each of the three spectral regions of light, red, green and blue. For this purpose, the light-sensitive layers are spectrally sensitized with suitable sensitizing dyes in known mannner. Blue-sensitive silver halide emulsion layers need not necessarily contain a spectral sensitizer since the intrinsic sensitivity of the silver halide is in many cases sufficient for the recording of blue light.

Each of the above-mentioned light-sensitive layers may consist of a single layer or it may comprise two or more silver halide emulsion partial layers in known manner, e.g. as in the so-called double layer arrangement (DE-C-1 121 470). Red-sensitive silver halide emulsion layers are conventionally arranged closer to the layer support than green-sensitive silver halide emulsion layers which in turn are arranged closer to the support than blue-sensitive layers, and a light-insensitive yellow filter layer is generally placed between the green-sensitive and the blue-sensitive layers although other arrangements could also be used. A light-insensitive interlayer containing substances to prevent accidental diffusion of developer oxidation products from one layer to another is generally placed between layers differing in their spectral sensitivity. When a photographic material contains several silver halide emulsion layers having the same spectral sensitivity, these layers may be arranged adjacent to one another or they may be separated by a light-sensitive layer having a different spectral sensitivity (DE-A-1 958 709, DE-A-2 530 645, DE-A-2 622 922).

Colour photographic recording materials for the production of multicolour images conventionally contain colour producing compounds in spatial and spectral association to the silver halide emulsion layers of differing spectral sensitivities, in this case in particular colour couplers, to produce the different partial colour images in cyan, magenta and yellow.

By "spatial association" is meant that the colour coupler is situated in such spatial relationship to the silver halide emulsion layer that interaction between these two layers is possible to result in an imagewise correspondence between the silver image produced on development and the colour image produced from the colour coupler. This is generally achieved by incorporating the colour coupler in the silver halide emulsion itself or in an optionally light-insensitive layer of binder adjacent thereto.

By "spectral association" is meant that the spectral sensitivity of each of the light-sensitive silver halide emulsion layers and the colour of the partial colour image produced from the colour coupler spatially associated with said silver halide emulsion layer are related to each other so that a different colour of the particular partial colour image (e.g. cyan, magenta, yellow) is associated with each of the spectral sensitivities (red, green, blue).

Each of the silver halide emulsion layers which differ from one another in their spectral sensitization may have one or more colour couplers associated therewith. When several silver halide emulsion layers having the same spectral sensitivity are present, each of these layers may contain a colour coupler and the various colour couplers need not necessarily be identical, provided only that on colour development they give rise to at least approximately the same colour, normally a colour which is complementary to the colour of the light to which the particular silver halide emulsion layers are predominantly sensitive.

In preferred embodiments, therefore, red-sensitive silver halide emulsion layers have at least one non-diffusible colour coupler associated therewith for producing the cyan partial colour image, generally a coupler of the phenol or α-naphthol series; green-sensitive silver halide emulsion layers have at least one non-diffusible colour coupler associated therewith for producing the magenta partial colour image, normally a colour coupler of the 5-pyrazolone series, the indazolone series or the pyrazolotriazole series; blue-sensitive silver halide emulsion layers have at least one non-diffusible colour coupler associated therewith for producing the yellow partial colour image, generally a colour coupler containing an open chain ketomethylene group. Colour couplers of this type are known in large numbers and have been described in numerous Patent Specifications.

The couplers may be incorporated in the casting solution for the silver halide emulsion layers or other colloid layers in known manner. Oil soluble or hydrophobic couplers, for example, are preferably added to a hydrophilic colloid solution from a solution in a suitable coupler solvent (oil former), optionally in the presence of a wetting or dispersing agent. The hydrophilic casting solution may, of course, contain conventional additives in addition to the binder. The solution of the coupler need not be directly dispersed in the casting solution for the silver halide emulsion layer or other water-permeable layer but may advantageously first be dispersed in an aqueous, light-insensitive solution of a hydrophilic colloid, the resulting mixture being then mixed with the casting solution for the light-sensitive silver halide emulsion layer or some other water-permeable layer, optionally after removal of the low boiling organic solvent used, and the resulting mixture may then be applied.

In addition to the constituents mentioned above, the colour photographic recording material may contain further additives, e.g. anti-oxidants, dye stabilizers and substances which influence the mechanical and electrostatic properties. UV absorbent compounds are advantageously used in one or more of the layers contained in the recording material, preferably in one of the upper layers, to reduce or prevent the adverse effect of UV light on colour images produced with the colour photographic recording material according to the invention. Suitable UV absorbents are described, for example, in U.S. Pat. No. 3,253,921, DE-C-2 036 719 and EP-A-0 057 160.

The layers of the photographic material may be hardened in the usual manner, for example with hardeners containing at least two reactive oxirane, aziridine or acryloyl groups. The layers may also be hardened by the process described in DE-A-2 218 009. Furthermore, the photographic layers or colour photographic multilayered materials may be hardened with hardeners of the diazine, triazine or 1,2-dihydroquinoline series or with vinylsulphone type hardeners. Other suitable hardeners are disclosed in DE-A-2 439 551, DE-A-2 225 230 and DE-A-2 439 551 and in Research Disclosure 17 643, Chapter X. The stabilizing effect of the compounds according to the invention is particularly marked when instant hardeners are used.

By "instant hardeners" are meant compounds which cross-link suitable binders at such a rate that immediately after casting or at the latest after 24 hours, preferably after 8 hours, hardening has been completed to such an extent that no further changes in sensitometry and swelling of the layers occurs as a result of the cross-linking reaction. By "swelling" is meant the difference between the wet layer thickness and the dry layer thickness when the film is processed under aqueous conditions. (Photogr. Sci. Eng. 16 (1964), 275; Photogr. Sci. Eng. 16 (1972), 449).

These hardeners which react very rapidly with gelatine include, for example, carbamoyl pyridinium salt, which presumably are capable of reacting with free carboxyl groups of the proteinaceous binder so that the carboxyl groups are enabled to react with free amino groups to form peptide bonds and undergo cross-linking.

Compounds corresponding to the following general formulae are examples of suitable instant hardeners:

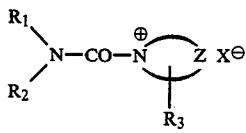 (a)

wherein
$R_1$ denotes alkyl, aryl or aralkyl,
$R_2$ has the same meaning as $R_1$ or denotes alkylene, arylene, aralkylene or alkaralkylene, in which the second bond is linked to a group of the formula

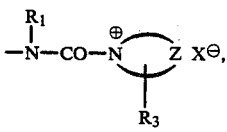

or
$R_1$ and $R_2$ together denote the atoms required for completing an optionally substituted heterocyclic ring, for example a piperidine, piperazine or morpholine ring, which ring may be substituted, e.g. by $C_1$-$C_3$-alkyl or by halogen,
$R_3$ denotes hydrogen alkyl, aryl, alkoxy, $NR_4$—$COR_5$, $(CH_2)_m$—$NR_8 R_9$, $(CH_2)_n$—$CONR_{13}R_{14}$ or

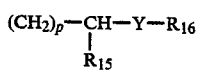

or it denotes a bridging member or a direct bond to a polymer chain, in which groups,
$R_4$, $R_6$, $R_7$, $R_9$, $R_{14}$, $R_{15}$, $R_{17}$, $R_{18}$ and $R_{19}$ denote hydrogen or $C_1$-$C_4$-alkyl.
$R_5$ denotes hydrogen, $C_1$-$C_4$-alkyl or $NR_6R_7$,
$R_8$ denotes $COR_{10}$,
$R_{10}$ denotes $NR_{11}R_{12}$,
$R_{11}$ denotes $C_1$-$C_4$-alkyl or aryl, in particular phenyl,
$R_{12}$ denotes hydrogen $C_1$-$C_4$-alkyl or aryl, in particular phenyl,
$R_{13}$ denotes hydrogen, $C_1$-$C_4$-alkyl or aryl, in particular phenyl,
$R_{16}$ denotes hydrogen, $C_1$-$C_4$-alkyl, $COR_{18}$ or $ONHR_{19}$,
m denotes a number from 1 to 3,
n denotes a number from 0 to 3,
p denotes a number from 2 to 3 and
Y denotes O or $NR_{17}$, or
$R_{13}$ and $R_{14}$ together denote the atoms required for completing an optionally substituted heterocyclic ring, for example a piperidine, piperazine or morpholine ring, which ring may be substituted, e.g. by $C_1$-$C_3$-alkyl or by halogen,
Z denotes the carbon atoms required for completing a 5- or 6-membered aromatic heterocyclic ring optionally carrying a condensed benzene ring, and $X^\ominus$ denotes an anion, this anion being absent if an anionic group is already attached to the remainder of the molecule;

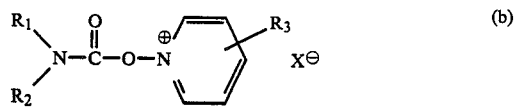 (b)

wherein $R_1$, $R_2$, $R_3$ and $X^\ominus$ have the meaning indicated for formula (a);

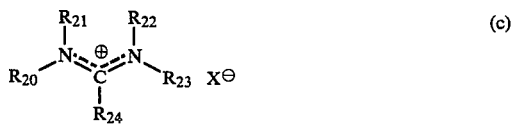 (c)

wherein
$R_{20}$, $R_{21}$, $R_{22}$ and $R_{23}$ denote $C_1$-$C_{20}$-alkyl, $C_6$-$C_{20}$-aralkyl or $C_5$-$C_{20}$-aryl, each of which may be unsubstituted or substituted by halogen, sulpho, $C_1$-$C_{20}$-alkoxy or N,N-di-$C_1$-$C_4$-alkyl-substituted carbamoyl, and aralkyl and aryl may also be substituted by $C_1$-$C_{20}$-alkyl,
$R_{24}$ denotes a group which can be split off by a nucleophilic agent, and
$X^\ominus$ has the meaning indicated for formula (a), and 2 or 4 of the substituents $R_{20}$, $R_{21}$, $R_{22}$ and $R_{23}$ together with a nitrogen atom or with the group

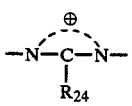

may be joined together to form one or two saturated 5—7-membered rings, optionally with the inclusion of further hetero atoms such as O or N;

 (d)

wherein
$R_{25}$ denotes $C_1$-$C_{10}$-alkyl, $C_5$-$C_8$-cycloalkyl, $C_3$-$C_{10}$-alkoxyalkyl or $C_7$-$C_{15}$-aralkyl,
$R_{26}$ has the meaning indicated for $R_{25}$ or stands for a group corresponding to the formula

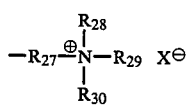

in which
$R_{27}$ denotes $C_2$-$C_4$-alkylene and
$R_{28}$, $R_{29}$ and $R_{30}$ denote $C_1$-$C_6$-alkyl, and one of the groups $R_{28}$, $R_{29}$ or $R_{30}$, may be substituted by a carbamoyl group or a sulpho group and two of the groups, $R_{28}$, $R_{29}$ and $R_{30}$, together with the nitrogen atom, may be joined together to form an optionally substituted heterocyclic ring, for example a pyrrolidine, piperazine or morpholine ring, which ring may be substituted, e.g. by $C_1$-$C_3$-alkyl or halogen, and
$X^\ominus$ has the meaning indicated for formula (a);

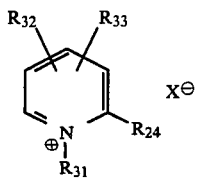
(e)

wherein $X^\ominus$ has the meaning indicated for formula (a), $R_{24}$ has the meaning indicated for formula (c), $R_{31}$ denotes $C_1$–$C_{10}$-alkyl, $C_6$–$C_{15}$-aryl or $C_7$–$C_{15}$-aralkyl, each of which may be unsubstituted or substituted by carbamoyl, sulphamoyl or sulpho, $R_{32}$ and $R_{33}$ denote hydrogen halogen, acylamino, nitro, carbamoyl, ureido, alkoxy, alkyl, alkenyl, aryl or aralkyl or together they denote the remaining members of a ring which is condensed with the pyridinium ring, in particular a benzo ring, and $R_{24}$ and $R_{31}$ may be joined together if $R_{24}$ is a sulphonyloxy group;

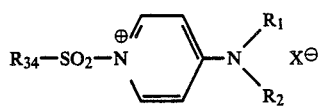
(f)

wherein $R_1$, $R_2$ and $X^\ominus$ have the meanings indicated for formula (a) and $R_{34}$ denotes $C_1$–$C_{10}$-alkyl, $C_6$–$C_{14}$-aryl or $C_7$–$C_{15}$-aralkyl;

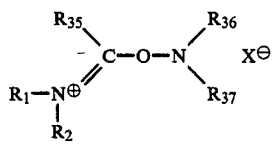
(g)

wherein $R_1$, $R_2$ and $X^\ominus$ have the meanings indicated for formula (a), $R_{35}$ denotes hydrogen, alkyl, aralkyl, aryl, alkenyl, $R_{38}O$, $R_{39}R_{40}N$, $R_{41}R_{42}C{=}N$ or $R_{38}S$, $R_{36}$ and $R_{37}$ denote alkyl, aralkyl, aryl, alkenyl,

, $R_{44}$—$SO_2$ or $R_{45}$—$N{=}N$, or $R_{36}$ and $R_{37}$ together with the nitrogen atom denote the remaining members of a heterocyclic ring or the group

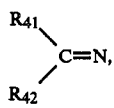

and $R_{38}$, $R_{39}$, $R_{40}$, $R_{41}$, $R_{42}$, $R_{43}$, $R_{44}$ and $R_{45}$ denote alkyl, aralkyl or alkenyl and $R_{41}$ and $R_{42}$ may in addition denote hydrogen, $R_{39}$ and $R_{40}$ together or $R_{41}$ and $R_{42}$ together may also denote the remaining members of a 5- or 6-membered, saturated carbocyclic or heterocyclic ring;

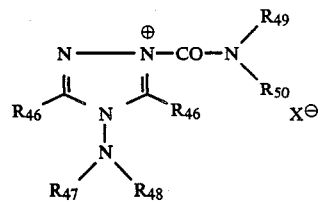
(h)

wherein $R_{46}$ denotes hydrogen, alkyl or aryl, $R_{47}$ denotes acyl, carbalkoxy, carbamoyl or aryloxycarbonyl;

$R_{48}$ denotes hydrogen or $R_{47}$, $R_{49}$ and $R_{50}$ denote alkyl, aryl or aralkyl or together with the nitrogen atom they denote the remaining members of an optionally substituted heterocyclic ring, for example a piperidine, piperazine or morpholine ring, which ring may be substituted, e.g. with $C_1$–$C_3$-alkyl or with halogen, and $X^\ominus$ has the meaning indicated for formula (a);

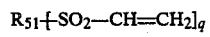
(i)

wherein $R_{51}$ denotes an optionally substituted heteroaromatic ring containing at least q ring carbon atoms and at least one ring-O-, ring-S- or ring-N- atom and q stands for an integar $\geq 2$.

The heteroaromatic ring denoted by $R_{51}$ may be, for example, a triazole, thiadiazole, oxadiazole, pyridine, pyrrole, quinoxaline, thiophene, furan, pyrimidine or triazine ring. In addition to the at least two vinylsulphonyl groups, it may contain further substituents and optionally condensed benzene rings which may in turn be substituted. Examples of heteroaromatic rings ($R_{51}$) are represented by the following formulae:

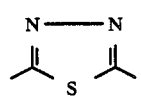

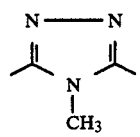

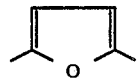

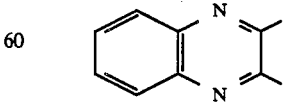

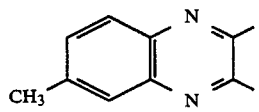

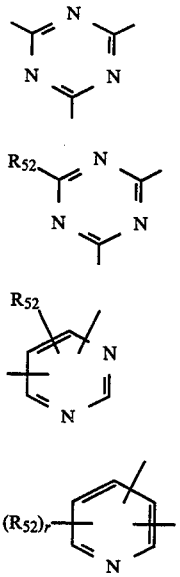

wherein
r represents a number from 0 to 3 and
$R_{52}$ denotes $C_1-C_4$-alkyl, $C_1-C_4$-alkoxy or phenyl.

The compounds described in Japanese Offenlegungsschriften Nos. 38 540/75, 93 470/77, 43 353/81 and 113 929/83 and in US-PS 3 321 313 are also suitable instant hardeners.

The alkyl group is in particular a $C_1-C_{20}$-alkyl group optionally substituted by halogen, hydroxyl, sulpho or $C_1-C_{20}$-alkoxy unless defined differently.

The aryl group, unless defined differently, is in particular a $C_6-C_{14}$-aryl group, optionally substituted by halogen, sulpho, $C_1-C_{20}$-alkoxy or $C_1-C_{20}$-alkyl. The aralkyl group, unless defined differently, is in particular a $C_7-C_{20}$-aralkyl group substituted by halogen, $C_1-C_{20}$-alkoxy, sulpho or $C_1-C_{20}$-alkyl. The alkoxy group is in particular a $C_1-C_{20}$-alkoxy group unless defined differently.

$X^\ominus$ is preferably a halide ion such as $Cl^\ominus$, $Br^\ominus$ or $BF_4^\ominus$, or $NO_3^\ominus$, $(SO_4^{2\ominus})_{\frac{1}{2}}$, $ClO_4^\ominus$, $CH_3OSO_3^\ominus$, $PF_6^\ominus$ or $CF_3SO_3^\ominus$.

The alkenyl group is in particular a $C_2-C_{20}$-alkenyl group; the alkylene group is in particular a $C_2-C_{20}$-alkylene group; the arylene group is in particular phenylene; the aralkylene group is in particular benzylene and the alkaralkylene group is in particular xylylene.

Suitable ring systems containing nitrogen, which may be denoted by Z, are shown on the previous page. The pyridine ring is preferred.

$R_{36}$ and $R_{37}$ together with the nitrogen atom to which they are attached denote in particular a pyrrolidine or piperdine ring having two oxo groups attached in the o- and o'-position, which ring may be benzocondensed, cyclohexeno condensed or [2,2,1]-bicyclohexenocondensed.

The acyl group is in particular a $C_1-C_{10}$-alkylcarbonyl group or a benzoyl group; the carbalkoxy group is in particular a $C_1-C_{10}$-alkoxycarbonyl group; the carbamoyl group is in particular a mono- or di-$C_1-C_4$-alkylaminocarbonyl group; and carbaroxy is in particular phenoxycarbonyl.

Examples of groups $R_{24}$ which can be split off by nucleophilic agents include halogen atoms, $C_1-C_{15}$-alkylsulphonyloxy groups, $C_7-C_{15}$-aralkylsulphonyloxy groups, $C_6-C_{15}$arylsulphonyloxy groups and 1-pyridinyl groups.

For production of the colour photographic images, the colour photographic recording material according to the invention is developed with a colour developer compound. The colour developer compound used may be any developer compound which is capable of reacting in the form of its oxidation product with colour couplers to form azomethine dyes. Suitable colour developer compounds include aromatic compounds of the p-phenylenediamine series containing at least one primary amino group, e.g. N,N-dialkyl-p-phenylenediamines such as N,N-diethyl-p-phenylenediamine, 1-(N-ethyl-N-methyl-sulphonamidoethyl)-3-methyl-p-phenylenediamine, 1-(N-ethyl-N-hydroxyethyl-3-methyl-p-phenylenediamine and 1-(N-ethyl-N-methoxyethyl)-3-methyl-p-phenylenediamine.

After colour development, the material is bleached and fixed in the usual manner. Bleaching and fixing may be carried out separately or together. The usual bleaching agents may be used, e.g. $Fe^{3+}$ salts and $Fe^{3+}$ complex salts such as ferricyanides, dichromates, water-soluble cobalt complexes, etc. Iron-III complexes of aminopolycarboxylic acids are particularly preferred, in particular e.g. ethylenediaminotetracetic acid, N-hydroxyethylethylenediaminotriacetic acid, alkyliminodicarboxylic acids and corresponding phosphonic acids. Persulphates are also suitable bleaching agents.

Black-and-white materials according to this invention contain light-sensitive silver halide, calculated as $AgNO_3$, in a quantity of from 1.5 to 15 g of $AgNO_3/m^2$.

From 1–12 mol-% of the bromide may be replaced by silver iodide. From 2–10% by weight of an internally fogged emulsion may be added to the emulsion. The emulsion is spectrally sensitized to the 400 to 650 nm region of the spectrum. The emulsion layer may contain an azaindene, known stabilizers such as α-naphtholsulphonic acid and polyalkyleneoxides as development accelerators.

EXAMPLE 1

A highly sensitive silver iodobromide emulsion containing 5 mol-% of iodide and having a ratio by weight of gelatine to silver of 1.2 and containing 150 g of silver nitrate per kg of emulsion was ripened to optimum sensitivity with sulphur and gold compounds.

This emulsion was divided into several parts and the following substances were added per kg of emulsion:

| | |
|---|---|
| 4-Hydroxy-6-methyl-1,3,3a,7-tetraazaindene, 1% by weight aqueous-alkaline solution | 1.5 g |
| Saponin 10% by weight dissolved in water | 3.5 g | and the substances according to the invention (1% by weight dissolved in methanol) shown in the following Table in the quantities indicated.

The emulsions were then cast on a cellulose acetate support and dried (application 6.7 to 7.0 g calculated as silver nitrate per m²). Each emulsion layer was covered with a protective layer containing a hardener corresponding to the formula

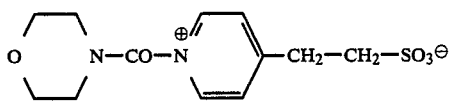

added in the given quantities to each sample. The following were added to the emulsion in the quantities given per kg of emulsion before casting:
75 g of 5% by weight gelatine solution;
109 g of an 11.1% by weight dispersion of the following magenta coupler:

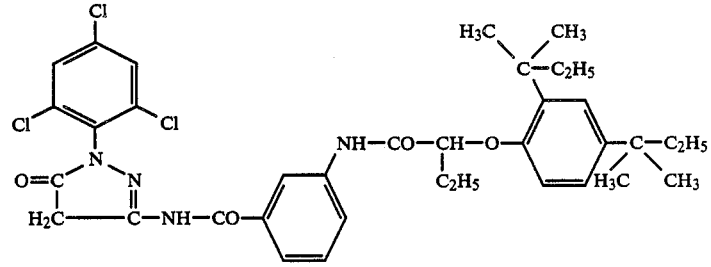

and a wetting agent, this protective layer being applied in a thickness corresponding to 2 g of gelatine per m² and 340 mg of hardener per m².

The samples were then exposed behind a grey wedge in a sensitometer and developed for 7 minutes at 20° C. in a developer having the following composition:

| p-Methylaminophenol | 3.5 g |
|---|---|
| Hydroquinone | 3.5 g |
| Sodium sulphite | 70.0 g |
| Sodium carbonate | 40.0 g |
| Potassium bromide | 2.0 g |
| Borax | 7.0 g |
| made up with water to 1 l. | |

The samples were then fixed in an acid fixing bath and washed in the usual manner. The results of the sensitometric tests are summarized in the following Table 2. It may be seen that the substances according to this invention reduce fogging and are therefore suitable as antifoggants even when the material is stored under conditions of elevated temperature or moisture.

TABLE 2

| Compound | Quantity Mol/mol AgNo₃ | $E_F$ | $S_F$ | $E_H$ | $S_H$ | $E_T$ | $S_T$ |
|---|---|---|---|---|---|---|---|
| Control | — | 29.7 | 0.24 | 31.7 | 0.23 | 28.3 | 0.14 |
| 1 | $1.7 \cdot 10^{-4}$ | 29.2 | 0.15 | 31.1 | 0.14 | 28.1 | 0.08 |
| 1 | $3.4 \cdot 10^{-4}$ | 28.5 | 0.10 | 30.4 | 0.10 | 27.3 | 0.07 |
| 3 | $1.7 \cdot 10^{-4}$ | 29.0 | 0.22 | 31.2 | 0.21 | 28.6 | 0.12 |
| 3 | $3.4 \cdot 10^{-4}$ | 28.6 | 0.18 | 29.7 | 0.19 | 28.1 | 0.12 |
| 7 | $1.7 \cdot 10^{-4}$ | 30.0 | 0.16 | 31.5 | 0.17 | 28.8 | 0.11 |
| 7 | $3.4 \cdot 10^{-4}$ | 29.9 | 0.15 | 30.5 | 0.15 | 28.9 | 0.11 |
| 8 | $1.7 \cdot 10^{-4}$ | 29.4 | 0.15 | 31.1 | 0.15 | 28.3 | 0.10 |
| 8 | $3.4 \cdot 10^{-4}$ | 29.1 | 0.12 | 30.2 | 0.14 | 28.7 | 0.09 |

$E_F$, $S_F$ = Sensitivity and fog of fresh sample
$E_H$, $S_H$ = sensitivity and fog after 3 d 60° C./34% humidity
$E_T$, $S_T$ = sensitivity and fog after 3 d 35° C./90% humidity
An increase in the given numerical values by three units corresponds to a doubling of the sensitivity.

EXAMPLE 2

1.2 g of 4-Hydroxy-6-methyl-1,3,3a,7-tetraazaindene in aqueous alkaline solution were added to 1 kg of a green sensitized silver iodobromide emulsion having a silver (calculated as silver nitrate)/gelatine ratio by weight of 1:0.4 and containing 0.91 mol of silver halide per kg of emulsion, including 5 mol-% of iodide, and the resulting emulsion was divided into several equal parts and solutions in methanol of the compounds according to the invention shown in the following Table 3 were added in the given quantities to each sample.

and wetting agent in aqueous solution and 1180 ml of water.

The emulsions were cast on the antihalation layer which consisted of a silver dispersion covering a cellulose acetate support. The quantity of emulsion applied corresponded to 2.2 to 2.3 g of AgNO₃/m².

A hardening layer was applied to each emulsion layer as described in Example 1.

The samples were examined fresh and after 3 days in a heating cupboard at 60° C. and 34% relative humidity and after 3 days in a tropical cupboard at 35° C. and 90% relative humidity.

The samples were then exposed in a sensitometer behind a step wedge and developed in the following developer at 38° C. for 3¼ minutes:

DEVELOPER

| Na₂ Salt of 1-hydroxyethane-1,1-diphosphonic acid | 2 g |
|---|---|
| Ethylenediamino-N,N,N',N'—tetracetic acid | 2 g |
| Potassium carbonate | 34.1 g |
| Sodium bicarbonate | 1.55 g |
| Sodium disulphite | 0.28 g |
| Sodium sulphite | 3.46 g |
| Potassium bromide | 1.34 g |
| Hydroxylamine sulphate | 2.4 g |
| 4-Amino-3-methyl-N—ethyl-N—(β-hydroxyethyl)-aniline | 4.7 g | made up with water to 1 l.
Processing continued in the following baths:

| Short stop bath | 1 minute at 38° C.; |
|---|---|
| Bleaching bath | 3¼ minutes at 38° C.; |
| Washing | 3½ minutes at 38° C. |
| Fixing bath | 3¼ minutes at 38° C.; |
| Washing | 5 minutes at 38° C. |

The short stop bath, bleaching bath and fixing bath were of the type conventionally used (British Journal of Photography, 1974, pages 597 and 598).

The results obtained are shown in Table 3.

The substances reduce the high fog without significantly reducing the sensitivity or the gradation and they improved the storage stability of the photographic material.

By contrast, the known thiopyrimidine derivatives V3 and V4 are less effective in reducing fogging and reduce the sensitivity to a greater extent.

TABLE 3

| Compound No. | Mol/100 g AgNo$_3$ | $E_F$ | $S_F$ | $E_H$ | $S_H$ | $E_T$ | $S_T$ |
|---|---|---|---|---|---|---|---|
| Control | — | 35.5 | 0.22 | 34.4 | 0.17 | 32.3 | 0.14 |
| 1 | $1.7 \cdot 10^{-4}$ | 35.1 | 0.15 | 34.1 | 0.12 | 31.9 | 0.11 |
| 1 | $3.4 \cdot 10^{-4}$ | 34.9 | 0.13 | 33.9 | 0.11 | 31.5 | 0.11 |
| 5 | $1.7 \cdot 10^{-4}$ | 34.9 | 0.16 | 33.8 | 0.11 | 33.5 | 0.13 |
| 5 | $3.4 \cdot 10^{-4}$ | 34.6 | 0.16 | 33.6 | 0.12 | 33.5 | 0.13 |
| 7 | $1.7 \cdot 10^{-4}$ | 34.9 | 0.17 | 33.9 | 0.12 | 32.0 | 0.14 |
| 7 | $3.4 \cdot 10^{-4}$ | 34.6 | 0.13 | 33.6 | 0.11 | 32.1 | 0.12 |
| 8 | $1.7 \cdot 10^{-4}$ | 34.6 | 0.14 | 33.6 | 0.11 | 33.4 | 0.12 |
| 8 | $3.4 \cdot 10^{-4}$ | 34.4 | 0.13 | 33.4 | 0.10 | 32.5 | 0.11 |
| V3 | $1.7 \cdot 10^{-4}$ | 35.1 | 0.18 | 34.0 | 0.12 | 32.0 | 0.13 |
| V3 | $3.4 \cdot 10^{-4}$ | 34.5 | 0.17 | 33.9 | 0.12 | 32.0 | 0.13 |
| V4 | $1.7 \cdot 10^{-4}$ | 34.9 | 0.18 | 33.9 | 0.13 | 32.1 | 0.14 |
| V4 | $3.4 \cdot 10^{-4}$ | 34.6 | 0.18 | 33.6 | 0.12 | 31.9 | 0.13 |

For the meaning of $E_F$, $S_F$, $E_H$, $S_H$, $E_T$ and $S_T$ see Table 2.

EXAMPLE 3

A highly sensitive silver chlorobromide emulsion containing 20 mol-% of chloride and having a gelatine/silver ratio of 1.0 and containing 200 g of silver nitrate per kg of emulsion was ripened to optimum sensitivity with sulphur compounds.

The ripened emulsion was then sensitized to the blue region of the spectrum and subdivided into several parts to which the substances shown in the following Table were added in the form of 1% by weight solutions.

1 mMol of yellow coupler in the form of an emulsion per 2.6 mMol of Ag and a wetting agent were then added to the blue-sensitive emulsion.

The emulsion was then cast on a paper support which had been coated with polyethylene on both sides (application 0.45 g AgNO$_3$/m$^2$) and was dried. A protective layer containing a hardener corresponding to the following formula

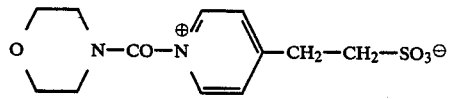

and a wetting agent were applied to each emulsion to form a layer thereon containing 1.8 g of gelatine/m$^2$ and 300 mg of hardener/m$^2$.

The samples were then exposed in a sensitometer behind a grey wedge and colour developed (Ektaprint 2). A second sample of the same emulsion cast on a support was stored in a heating cupboard for 2 days before development. The sensitometric data are shown in the following Table:

| Cast emulsion | Compound | mMol per mol of Ag | Fresh Rel. sensitivity | $D_{min}$ | Heating cupboard Rel. sensitivity | $\Delta D_{min}$ |
|---|---|---|---|---|---|---|
| 1 | — | — | 100 | 0.238 | 113 | 0.147 |
| 2 | 1 | 0.27 | 98 | 0.133 | 118 | 0.003 |
| 3 | 1 | 0.46 | 97 | 0.119 | 115 | 0.002 |
| 4 | V1 | 0.26 | 105 | 0.156 | 124 | 0.017 |
| 4 | V1 | 0.44 | 102 | 0.137 | 119 | 0.020 |
| 6 | V3 | 0.36 | 99 | 0.148 | 116 | 0.018 |

EXAMPLE 4

A highly sensitive silver chloride emulsion having a gelatine/silver ratio of 1.0 and a silver nitrate content of 200 g per kg of emulsion was optimally ripened with sulphur and gold compounds. The ripened emulsion was then sensitized to the blue region of the spectrum and divided into several parts and the compounds (see Table 2) were added as 1% by weight solutions.

Further treatment was carried out as in Example 3 except that the second exposed sample was not stored in the heating cupboard but stored for 6 weeks at room temperature. The sensitometric results are shown in the following

TABLE

| Casting liquid | Compound | mMol per mol of Ag | Fresh Rel. sensitivity | $D_{min}$ | 6 weeks storage Rel. sensitivity | $\Delta D_{min}$ |
|---|---|---|---|---|---|---|
| 7 | — | — | fog* | 0.625 | — | 0.109 |
| 8 | 1 | 0.27 | 100 | 0.249 | 102 | 0.008 |
| 9 | 1 | 0.46 | 99.5 | 0.199 | 100 | 0.001 |
| 10 | V1 | 0.44 | fog* | 0.736 | fog* | 0.105 |
| 11 | V4 | 0.42 | 102 | 0.295 | 102 | 0.034 |

*"Fog" denotes that the material is completely unusable.

EXAMPLE 5

A silver chlorobromide emulsion containing 20 mol-% of chloride was prepared as in Example 3 and sensitized to the blue region of the spectrum. The emulsion was then divided into three parts and the compounds shown in the following Table were added as 1% by weight solutions. After the addition of yellow coupler, the emulsion was cast on a paper support (application 1.5 g AgNO$_3$/m$^2$) which had been coated with polyethylene on both sides, and the emulsion on the support was then dried. A protective layer was cast over the emulsion as in Example 3. One sample of each casting was stored for 24 hours at 20° C. and 50% relative humidity and another sample of each casting was stored for 24 hours at 20° C. and 85% relative humidity. The samples were exposed after one sample had been equilibrated to 50% relative humidity. The sensitivities were measured after color development. As may be seen from the Table, when the compound according to the invention is used there is no loss in sensitivity when the samples are stored under moist conditions before exposure.

| Casting liquid | Compound | mMol per mol of Ag | 50% rel. humidity Rel. sensitivity | 85% rel. humidity Rel. sensitivity |
|---|---|---|---|---|
| 12 | V2 | 0.37 | 100 | 97 |
| 13 | 1 | 0.27 | 100 | 99 |
| 14 | 1 | 0.46 | 100 | 100 |

EXAMPLE 6

An AgClBr emulsion containing 25 mol-% of AgCl and having an average grain diameter of 45 μm was prepared by partial conversion of an AgCl emulsion. After desalting by known methods, the emulsion is dispersed in gelatine solution so that a gelatine/AgNO$_3$ ratio of 1 and a silver content of 100 g of AgNO$_3$ per kg of emulsion result. The emulsion is then chemically ripened with sodium thiosulphate.

Thereafter, the emulsion is optically sensitized to the red region of the spectrum and stabilizers are then added. After the addition of Ag-coupler emulsion, the whole emulsion is cast on a PE support, hardened with hardener and developed in a colour developer for 3½ minutes after exposure. A proportion of the samples packaged under light- and airtight conditions is subjected to a heat treatment before exposure to test the stability of the photographic material to the influence of heat, moisture and prolonged storage.

C. for 72 hours. After exposure, the samples are developed for 45 seconds at 35° C. (RA-4-process).

TABLE 6

| Casting liquid | Compound | mMol/mol of Ag | $D_{min}$ | $D_{min}$ 3d 54° C. | Δ $D_{min}$ | rel. sensitivity | rel. sensitivity 3d 54° C. | Δ E rel. |
|---|---|---|---|---|---|---|---|---|
| 23 | — | 0.28 | 0.136 | 0.306 | +0.170 | 1.00 | 1.060 | +0.060 |
| 24 | 1 | 0.27 | 0.123 | 0.182 | +0.050 | 0.979 | 0.949 | −0.030 |
| 25 | V1 | 0.26 | 0.158 | 0.293 | +0.135 | 0.818 | 0.973 | +0.155 |
| 26 | V4 | 0.36 | 0.140 | 0.283 | +0.140 | 0.967 | 0.988 | +0.243 |

TABLE 4

| Casting liquid | Compound | mMol/mol of Ag | $D_{min}$ | $D_{min}$ 2d 60° C. | Δ $D_{min}$ | rel. sensitivity | rel. sensitivity 2d 60° C. | Δ E rel. |
|---|---|---|---|---|---|---|---|---|
| 15 | — | 0.28 | 0.145 | 0.211 | +0.066 | 1.00 | 1.128 | +0.128 |
| 16 | 1 | 0 27 | 0.122 | 0.169 | +0.047 | 0.942 | 0.922 | −0.020 |
| 17 | V1 | 0.26 | 0.221 | 0.340 | +0.119 | 0.974 | 1.068 | +0.094 |
| 18 | V4 | 0.36 | 0.139 | 0.201 | +0.062 | 0.928 | 1.042 | +0.114 |

The compound according to the invention is distinguished by the low minimum density, the slight change in minimum density on heat treatment and the slight change in sensitivity.

EXAMPLE 7

An AgClBr emulsion containing 25 mol-% of chloride and having an average grain diameter of 0.43 μm is prepared by the double jet process with control of the pAg. Growth of the silver halide grains takes place layerwise while the ratio of chloride to bromide ions supplied varies and a silver complex forming agent is added to prevent the formation of new crystallisation nuclei. Desalting is followed by dispersion, chemical sensitization and optical sensitization as in Example 6. Addition of the stabilizers and couplers and subsequent treatment of the samples are carried out as in Example 1.

The results are shown in Table 5.

TABLE 5

| Casting liquid | Compound | mMol/mol of Ag | $D_{min}$ | $D_{min}$ 2d 60° C. | Δ $D_{min}$ | rel. sensitivity | rel. sensitivity 2d 60° C. | Δ E rel. |
|---|---|---|---|---|---|---|---|---|
| 19 | — | 0.28 | 0.136 | 0.173 | +0.037 | 1.00 | 0.938 | −0.062 |
| 20 | 1 | 0.27 | 0.107 | 0.111 | +0.004 | 0.935 | 0.915 | −0.020 |
| 21 | V1 | 0.26 | 0.148 | 0.228 | +0.080 | 1.06 | 1.16 | +0.100 |
| 22 | V4 | 0.36 | 0.138 | 0.182 | +0.044 | 0.98 | 1.04 | +0.60 |

EXAMPLE 8

An AgCl emulsion doped with 0–3 mol-% of AgBr and 0–0.5 mol-% of AgI and having a grain diameter of 0.38 μm is prepared by the double jet process with conrolled pAg and the addition of a silver complex forming agent. After desalting and dispersion, the emulsion is chemically sensitized with $NH_4Au(SCN)_2$ and thiosulphate. Optical sensitization, addition of the stabilizing compounds and coating are carried out as in Example 6. A portion of the samples is heat treated at 54°

The cast emulsion 24 shows the least minimum density and the least change in minimum density and in sensitivity after heat treatment.

We claim:

1. Photographic recording material containing at least one silver halide emulsion layer and optionally other layers and an antifoggant corresponding to the formula

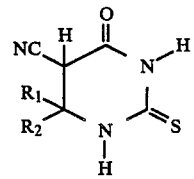

wherein $R_1$ and $R_2$ denote an optionally substituted alkyl group with 1 to 8 carbon atoms, an optionally substituted alkenyl group with 2 to 5 carbon atoms, an optionally substituted cycloalkyl group with 5 or 6 carbonatoms or an optionally substituted aryl group or together they denote the ring members for forming a 5- or 6-membered cycloalkyl or cycloalkenyl group.

2. Photographic recording material according to claim 1, wherein $R_1$ denotes $C_1$–$C_4$-alkyl and $R_2$ denotes $C_1$–$C_4$-alkyl, phenyl, cyclohexyl, di-$C_1$–$C_4$-alkylamino-$C_1$–$C_4$-alkyl, $C_1$–$C_4$-alkoxy-$C_1$–$C_4$-alkyl, $C_1$–$C_4$-alkylthio-$C_1$–$C_4$-alkyl or allyl or $R_1$ and $R_2$ together denote tetramethylene or pentamethylene.

* * * * *